US00PP18688P2

(12) United States Plant Patent
Klaveren

(10) Patent No.: US PP18,688 P2
(45) Date of Patent: Apr. 1, 2008

(54) ***HYDRANGEA* PLANT NAMED 'ZEBRA'**

(50) Latin Name: *Hydrangea macrophylla*
Varietal Denomination: Zebra

(76) Inventor: Arie D. Klaveren, Hoofdweg 149, De Kwakel (NL), 1424 PE ( * ) Notice: Subject to any disclaimer, the term of this patent is extended or adjusted under 35 U.S.C. 154(b) by 0 days.

(21) Appl. No.: 11/508,613

(22) Filed: Aug. 23, 2006

(51) Int. Cl.
*A01H 5/00* (2006.01)

(52) U.S. Cl. ..... Plt./250

(58) Field of Classification Search ..... Plt./250
See application file for complete search history.

*Primary Examiner*—Kent Bell
*Assistant Examiner*—June Hwu
(74) *Attorney, Agent, or Firm*—Penny J. Aguirre

(57) ABSTRACT

A new cultivar of *Hydrangea macrophylla* named 'Zebra', a sport of *Hydrangea macrophylla* 'Schneeball' that is characterized by its pure white colored inflorescences that are borne on strong, nearly black flower stems.

2 Drawing Sheets

Genus/species: *Hydrangea macrophylla.*
Varietal denomination: 'Zebra'.

BACKGROUND OF THE INVENTION

The present invention relates to a new and distinct cultivar of *Hydrangea macrophylla* and will be referred to hereafter by its cultivar name, 'Zebra'. 'Zebra' represents a new Bigleaf *Hydrangea,* a deciduous shrub grown for landscape use and for use as a potted plant.

'Zebra' was discovered by the inventor as a naturally occurring branch mutation of *Hydrangea macrophylla* 'Schneeball' (not patented) in June 2003 in De Kwakel, The Netherlands. The inventor produces approximately 10,000 plants of the parent variety 'Schneeball' in his nursery annually and discovered one branch on a single plant that was nearly black in coloration; stem cuttings of the mutant branch resulted in the new cultivar, 'Zebra'.

Asexual reproduction of the new cultivar was first accomplished by softwood stem cuttings in De Kwakel, The Netherlands in July 2003 by the inventor. The characteristics of this cultivar have been determined to be stable and are reproduced true to type in successive generations.

SUMMARY OF THE INVENTION

The following traits have been repeatedly observed and represent the characteristics of the new cultivar. These attributes in combination distinguish 'Zebra' as a unique cultivar of *Hydrangea macrophylla.*

1. 'Zebra' exhibits stems that are nearly black in color.
2. 'Zebra' exhibits pure white flowers in compound corymbs in early summer.
3. 'Zebra' exhibits very strong stems.
4. 'Zebra' is hardy at least to U.S.D.A. Zone 6.

The only close comparison plant to the new cultivar of *Hydrangea* is the parent plant, *Hydrangea macrophylla* 'Schneeball'. 'Zebra' is similar to 'Schneeball' in foliage, flower, and habit characteristics, however 'Zebra' differs in having nearly black stems whereas 'Schneeball' exhibits green stems.

BRIEF DESCRIPTION OF THE DRAWINGS

The photographs in the figures were taken of a one year-old plant of 'Zebra' as grown outdoors in a 15 cm container in De Kwakel, The Netherlands.

The photograph on the top of first sheet illustrates a plant of 'Zebra' in bloom and the stem color is illustrated.

The photograph on the bottom of the first sheet provides a close-up view of a leaf of 'Zebra'.

The photograph of the top of the second sheet provides a view of a fully open inflorescence and the photograph on the bottom of the second sheet is a close-up view of the flowers of 'Zebra'.

The colors in the photographs are as close as possible with the digital photography and printing techniques utilized and the color codes in the detailed botanical description more accurately describe the new *Hydrangea.*

BOTANICAL DESCRIPTION OF THE PLANT

The following is a detailed description of one year-old plants of the new cultivar as grown in 15 cm containers under ambient light, outdoors in De Kwakel, The Netherlands. Phenotypic differences may be observed with variations in environmental, climatic, and cultural conditions. The color determination is in accordance with the 2001 R.H.S. Colour Chart of The Royal Horticultural Society, London, England, except where general color terms of ordinary dictionary significance are used.

Botanical classification: 'Zebra' is a cultivar of *Hydrangea macrophylla.*
Commercial classification: Bigleaf *hydrangea,* Hortensia type.
Parentage: Naturally occurring branch sport of *Hydrangea machrophylla* 'Scheeball'.
General description:
*Blooming period.*—Early summer blooming.
*Plant habit.*—Broadly upright, deciduous shrub.
*Height and spread.*—Reaches about 45 cm in height and 34.5 cm width when mature.

*Cold hardiness.*—At least to U.S.D.A. Zone 6, colder zones have not been tested.

*Heat tolerance.*—Known to tolerate temperatures of at least 32° C.

*Culture.*—Grows best in most but well-drained, humus-rich soil in full sun or partial shade with protection from high winds.

*Diseases resistance.*—No susceptibility or resistance diseases known to effect *H. macrophylla* has been observed.

*Root description.*—Fine.

Growth and propagation:

*Propagation.*—Softwood stem cuttings.

*Time required for root development.*—About 3 weeks to fully develop in a liner as grown under greenhouse conditions at an average temperature of 20° C.

*Time required to produce a salable crop.*—About 12 months from propagation to a flowering plant in a 15 cm container.

*Growth rate and vigor.*—Moderate, growth rate is about 15 cm per month in spring.

Stem description:

*Stem shape.*—Round, solid.

*Stem strength.*—Strong.

*Stem color.*—N186C to 200A but darker.

*Stem size.*—Average of 25 cm (to base of inflorescence), average of 6 mm in width.

*Stem surface.*—Glabrous, glossy, sparsely covered with lenticels; about 8 per square cm, about 2.5 mm in length and 0.5 mm in width and 152A to 152B in color.

*Internode length.*—Average of 7.1 cm.

*Branching.*—A single dormant stem will produce an average of 4 lateral branches, sublateral branching is determined by pinching; 2 stems develop per pinched node.

Foliage description:

*Leaf shape.*—Ovate to broadly ovate.

*Leaf arrangement.*—Opposite.

*Leaf division.*—Simple.

*Leaf number.*—Average of 8 (4 pairs) per lateral branch.

*Leaf base.*—Obtuse.

*Leaf apex.*—Apiculate.

*Leaf margins.*—Serrated.

*Leaf venation.*—Penninerved, recessed on upper surface, color 144A to 144B on upper surface and 145 a to 145B on lower surface.

*Leaf size.*—Average of 9.1 cm in length and 7.3 cm in width.

*Leaf attachment.*—Petiolate.

*Leaf surface.*—Glabrous on upper and lower surface, slightly glossy on upper surface.

*Leaf color.*—Young foliage upper surface; 143A, young foliage lower surface; 143B to 143C, mature foliage upper surface; 137A to 137B, mature foliage lower surface; 137B to 137C to 143A.

*Petioles.*—Average of 1.7 cm in length and 3 mm in width, 144A to 144B in color.

Inflorescence description:

*Inflorescence type.*—Terminal compound globose corymb of rotate shaped flowers, about 77% of the flowers are sterile.

*Lastingness of inflorescence.*—Persistent but color is retained for about 4 weeks.

*Inflorescence number.*—One per lateral or sublateral stem if pinched.

*Inflorescence size.*—Average of 8.8 cm in height and 14.2 cm in diameter.

*Flower number.*—Numerous, average of 150 sterile flowers and 45 fertile flowers per inflorescence.

*Flower durability to stress.*—High.

*Flower fragrance.*—Faint.

*Time required to develop an inflorescence.*—Approximately 9 weeks after growth emerges when container grown.

*Flower aspect.*—Upright to outward.

*Flower size.*—Sterile flowers; average of 4.1 cm in diameter and 1.1 cm in depth, fertile flowers; average of 6 mm in diameter and 6 mm in depth.

*Flower buds.*—Average of 3.5 mm in length and 4 mm in width prior to opening, flattened globular in shape, 155D in color, flowers open in about 3 days from mature bud.

*Peduncles.*—Strong, average of 3.7 cm in length and 2.5 mm in width, held at about a 50° angle from vertical, 187A to 187B in color, surface is glabrous and shiny.

*Pedicels.*—Moderate strength, average of 3.5 cm in length on the sterile flowers and 1.9 cm in length on fertile flowers, 4 mm in width, held at about a 15 to 30° angle from vertical, 185B to 187C in color, surface is glabrous and shiny.

*Calyx.*—Campanulate in form, average of 2 cm in length and 4 mm in diameter.

*Petals.*—Average of 5, present on fertile flowers only, rotate in arrangement, ovate in shape, entire margin, acute apex, cuneate base, average of 1.5 mm in length and 1 mm in width, surface is glabrous and dull on both surfaces, color of upper and lower surface (opening and mature flowers) is 155A.

*Sepals.*—Average of 4 for sterile flowers, average of 5 for fertile flowers, un-fused, rotate in arrangement, glabrous and dull surface (both surfaces), orbicular to reniform in shape on sterile flowers, ovate in shape on fertile flowers, margin is entire on fertile flowers and crenate to bluntly serrate on sterile flowers, apex is rounded on sterile flowers and acute on fertile flowers, size on sterile flowers; average of 2.3 cm in length and 2.8 cm in width, size on fertile flowers; average of 3 mm in length and 2 mm in width, color remains the same through development on fertile and sterile flowers and on both sepal surfaces; pure white (whiter than any color on The R.H.S. colour chart but closest to 155A).

Reproductive organs: (fertile flowers):

*Stamens.*—Average of 9, anther is short oblong in shape, about 1 mm in length and 158D in color, filament is an average of 2.5 mm in length and whiter R.H.S. Color codes in color, pollen is low in quantity and 158D in color.

*Pistils.*—Average of 3, average of 1.2 mm in length, stigma is club-shaped and 155C in color, style is an average of 0.7 mm in length and 155C in color, ovary is inferior and 155C in color.

*Fruit and seed.*—Has not been observed under the conditions tested to date.

I claim:

1. A new and distinct cultivar of *Hydrangea* plant named 'Zebra' substantially as herein illustrated and described.

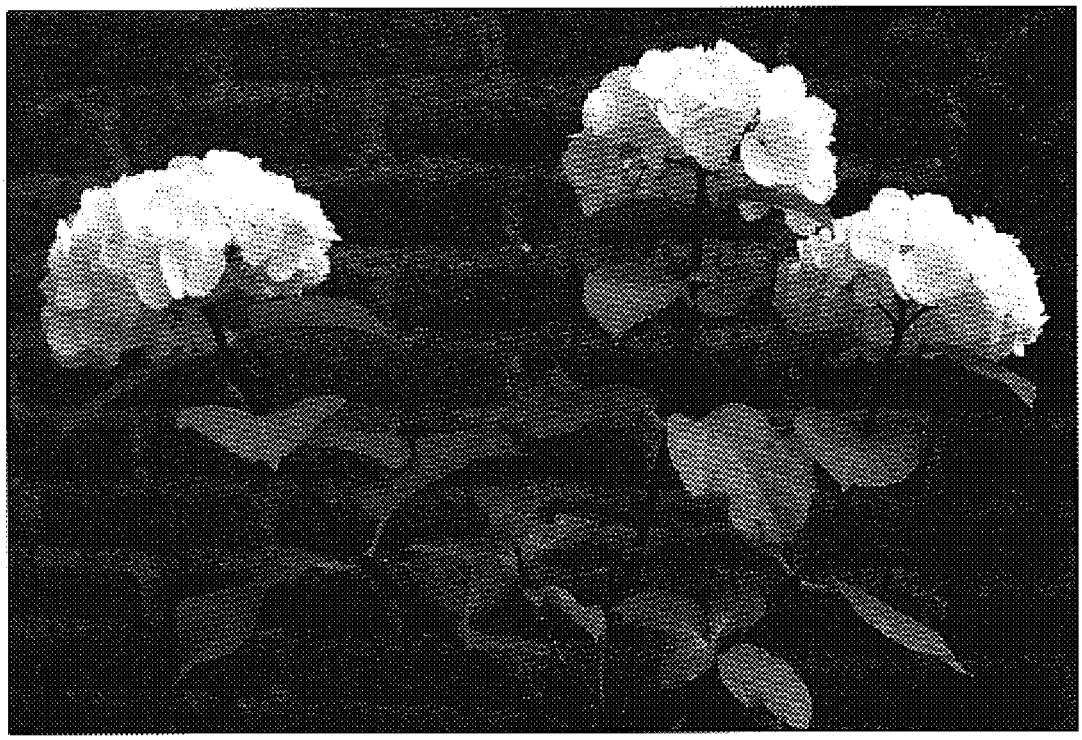
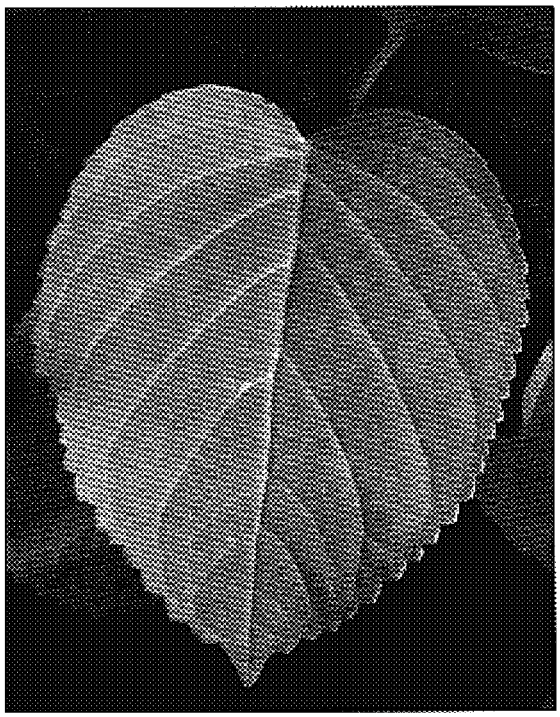

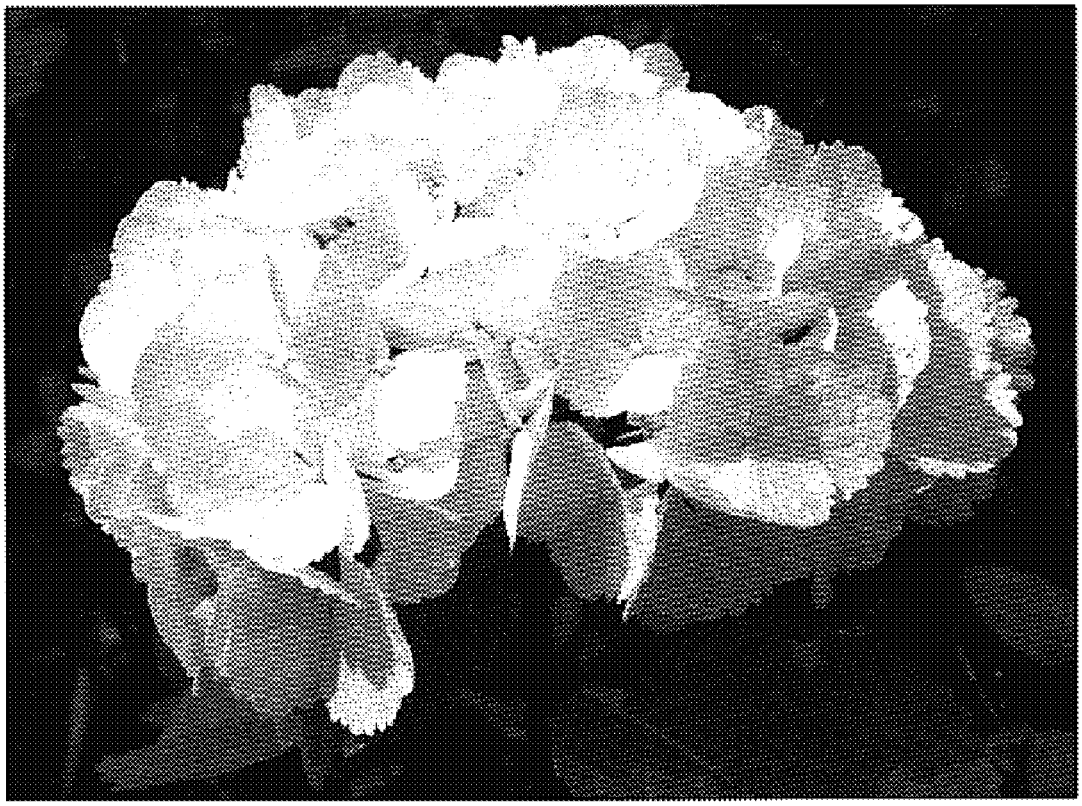
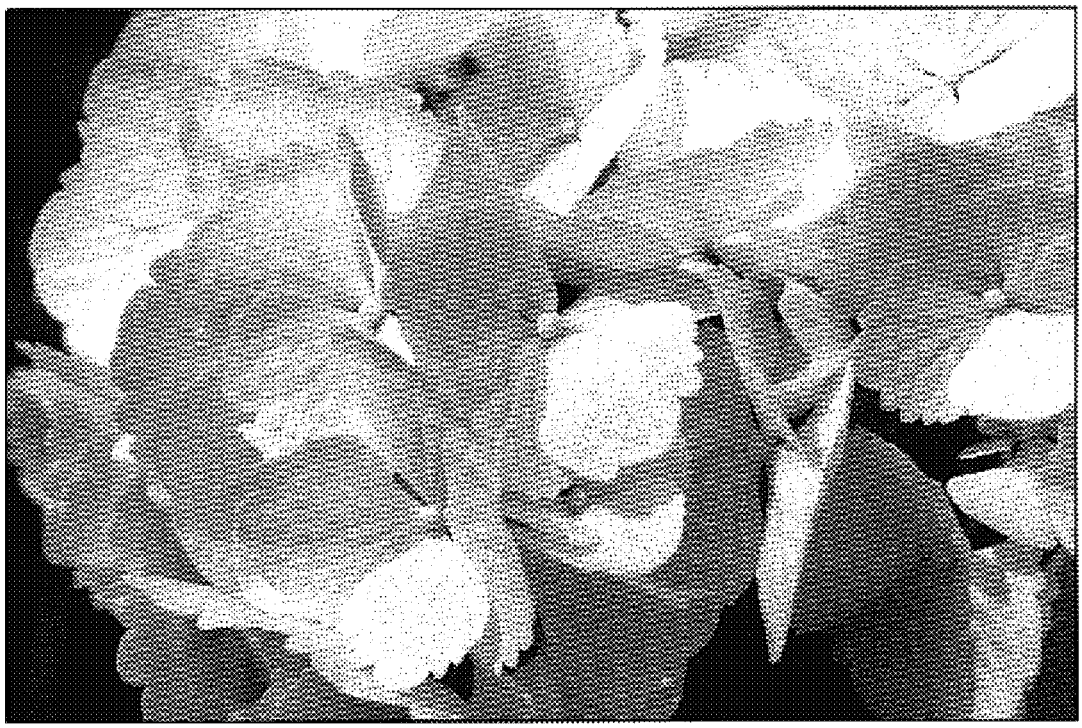

* * * * *